(12) United States Patent
Kawagishi et al.

(10) Patent No.: US 11,424,033 B2
(45) Date of Patent: Aug. 23, 2022

(54) INFORMATION PROCESSING APPARATUS, CONTROL METHOD THEREFOR, AND NON-TRANSITORY COMPUTER-READABLE STORAGE MEDIUM

(71) Applicant: CANON KABUSHIKI KAISHA, Tokyo (JP)

(72) Inventors: Masami Kawagishi, Kawasaki (JP); Hiroyuki Yamamoto, Chigasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 177 days.

(21) Appl. No.: 16/570,463

(22) Filed: Sep. 13, 2019

(65) Prior Publication Data

US 2020/0005942 A1    Jan. 2, 2020

Related U.S. Application Data

(63) Continuation of application No. PCT/JP2018/009404, filed on Mar. 12, 2018.

(30) Foreign Application Priority Data

Mar. 30, 2017    (JP) .............................. JP2017-068691

(51) Int. Cl.
*G16H 50/20*    (2018.01)
*G16H 30/40*    (2018.01)
(Continued)

(52) U.S. Cl.
CPC ........... *G16H 50/20* (2018.01); *A61B 6/5217* (2013.01); *G06T 7/0016* (2013.01); *G16H 30/40* (2018.01);
(Continued)

(58) Field of Classification Search
CPC ...... G16H 50/20; G16H 30/40; A61B 6/5217; G06T 7/0016
See application file for complete search history.

(56) References Cited

U.S. PATENT DOCUMENTS 6,058,322 A    5/2000 Nishikawa
8,949,171 B2    2/2015 Kawagishi
(Continued)

FOREIGN PATENT DOCUMENTS

EP    2551822 A2    1/2013
JP    2001-511372 A    8/2001
(Continued)

OTHER PUBLICATIONS

Shin, et al., "Learning to Read Chest X-Rays: Recurrent Neural Cascade Model for Automated Image Annotation", 2016 IEEE Conference On Computer Vision and Pattern Recognition (CVPR), pp. 2497-2506, DOI: 10.1109/CVPR.2016.274 ISBN: 978-1-4673-8851-1, Jun. 2016.

*Primary Examiner* — Edward Park
(74) *Attorney, Agent, or Firm* — Canon U.S.A., Inc. IP Division

(57) ABSTRACT

An information processing apparatus 100 comprising: first inference unit configured to perform a first inference to medical image data and obtain information related to a diagnostic name identified from the medical image data as a first inference result; and second inference unit configured to perform a second inference to the medical image data and the information related to the diagnostic name and obtain information related to an image finding as a second inference result.

18 Claims, 11 Drawing Sheets

(51) Int. Cl.
 *A61B 6/00* (2006.01)
 *G06T 7/00* (2017.01)
 *G06K 9/62* (2022.01)
(52) U.S. Cl.
 CPC ......... *G06K 9/6232* (2013.01); *G06K 9/6262* (2013.01); *G06T 2207/20081* (2013.01); *G06T 2207/20084* (2013.01); *G06T 2207/30061* (2013.01); *G06T 2207/30096* (2013.01)

(56) References Cited

U.S. PATENT DOCUMENTS

| | | | | |
|---|---|---|---|---|
| 2006/0111644 | A1* | 5/2006 | Guttag | A61B 5/4094 600/544 |
| 2007/0047574 | A1 | 3/2007 | Ling | |
| 2010/0014756 | A1 | 1/2010 | Kato | |
| 2012/0254101 | A1 | 10/2012 | Kawagishi | |
| 2013/0051646 | A1 | 2/2013 | Nakano | |
| 2015/0006447 | A1* | 1/2015 | Kawagishi | A61B 6/461 706/12 |
| 2016/0373443 | A1 | 12/2016 | Namiki | |

FOREIGN PATENT DOCUMENTS

| | | |
|---|---|---|
| JP | 2009-506664 A | 2/2009 |
| JP | 2009-205410 A | 9/2009 |
| JP | 2009-207585 A | 9/2009 |
| JP | 2010-017274 A | 1/2010 |
| JP | 2013-027635 A | 2/2013 |
| JP | 2013-172940 A | 9/2013 |
| JP | 2017-011392 A | 1/2017 |

\* cited by examiner

INFORMATION PROCESSING APPARATUS, CONTROL METHOD THEREFOR, AND NON-TRANSITORY COMPUTER-READABLE STORAGE MEDIUM

CROSS-REFERENCE TO RELATED APPLICATIONS

This application is a Continuation of International Patent Application No. PCT/JP2018/009404, filed Mar. 12, 2018, which claims the benefit of Japanese Patent Application No. 2017-068691, filed Mar. 30, 2017, both of which are hereby incorporated by reference herein in their entirety.

TECHNICAL FIELD

The present invention relates to an information processing apparatus, a control method therefor, and a non-transitory computer-readable storage medium.

BACKGROUND ART

A computer aided diagnosis (Computer Aided Diagnosis: CAD) system has been known in which a medical image is analyzed by a computing machine to present information that helps an interpretation by a doctor. PTL 1 describes a technology with which an image processing result corresponding to an objective assessment value is converted into an image finding corresponding to a subjective assessment value, and the image finding is obtained from the medical image to be presented to the doctor.

CITATION LIST

Patent Literature

PTL 1 Japanese Patent Laid-Open No. 2009-207585

However, according to the related-art technology, since the image finding is obtained from an image feature amount corresponding to the image processing result of the medical image, the obtained image finding is not matched with the image finding recalled from the medical image by the doctor in some cases.

An object of the present invention is to obtain information related to an image finding with which an interpretation by a doctor can be appropriately aided.

SUMMARY OF INVENTION

To achieve the above-described object, an information processing apparatus comprising: first inference unit configured to perform a first inference to medical image data and obtain information related to a diagnostic name identified from the medical image data as a first inference result; and second inference unit configured to perform a second inference to the medical image data and the information related to the diagnostic name and obtain information related to an image finding as a second inference result.

In addition, an information processing apparatus comprising: first inference unit configured to perform a first inference to medical image data and obtain information related to a likelihood of a malignancy of a disease identified from the medical image data as a first inference result; and second inference unit configured to perform a second inference to the medical image data and the information related to the likelihood of the malignancy of the disease and obtain information related to an image finding as a second inference result.

Further features of the present invention will become apparent from the following description of exemplary embodiments with reference to the attached drawings.

DESCRIPTION OF EMBODIMENTS

Hereinafter, embodiments for carrying out the present invention will be described by using the drawings.

First Embodiment

An information processing apparatus according to a first embodiment obtains an image finding of a medical image corresponding to a target of a medical diagnosis (interpretation).

It should be noted that, hereinafter, the medical image (which is synonymous with medical image data. The same applies hereinafter.) is set as a chest X-ray CT image, and the information processing apparatus obtains a diagnostic name (first inference result) on the basis of the medical image according to an interpretation of abnormal shading in the lung. Then, a case will be described as an example where an image finding (second inference result) related to the abnormal shading in the lung is obtained to the medical image and the diagnostic name. Of course, the target is not limited to this, and any of the diagnostic name, an image feature amount, the image finding, and the like which will be illustrated below is merely an example for describing steps of the processing of the information processing apparatus.

Figure 11:
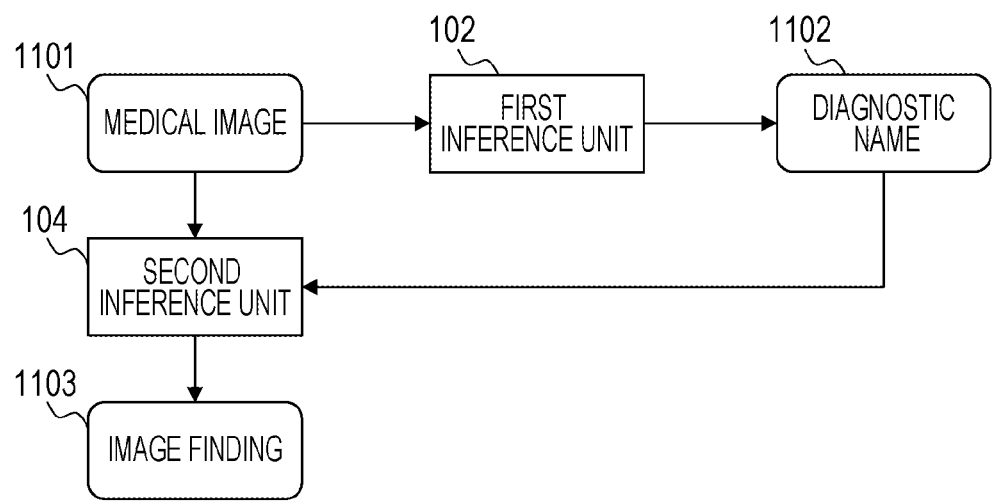
FIG. 11 illustrates an outline of the first embodiment.

First, an outline of the first embodiment will be described to FIG. 11. The information processing apparatus causes a first inference unit 102 included in the information processing apparatus to execute a first inference to a medical image 1101. According to this, the first inference unit 102 obtains a diagnostic name 1102 as the first inference result. That is, the first inference unit 102 infers the diagnostic name 1102 related to the abnormal shading captured in the medical image 1101 to the image feature amount of the medical image 1101 or the like.

Next, the information processing apparatus causes a second inference unit 104 included in the information processing apparatus to execute a second inference to the medical image 1101 and the diagnostic name 1102. According to this, the second inference unit 104 obtains an image finding 1103 as the second inference result. That is, the second inference unit 104 obtains the image finding 1103 related to the abnormal shading captured in the medical image 1101 to the image feature amount of the medical image 1101 or the like and further the diagnostic name 1102 obtained by the first inference unit 102.

When the information processing apparatus is operation as described above, the second inference unit 104 can obtain the image finding matched with the image finding recalled from the medical image by a doctor. In addition, since the diagnostic name corresponding to the first inference result is used for the second inference together with the medical image, it becomes possible to obtain the image finding having a high probability of being matched with the image finding that may be added to an interpretation report in a case where the doctor assumes the diagnostic name to perform the interpretation. Hereinafter, this detail will be described.

Figure 1:
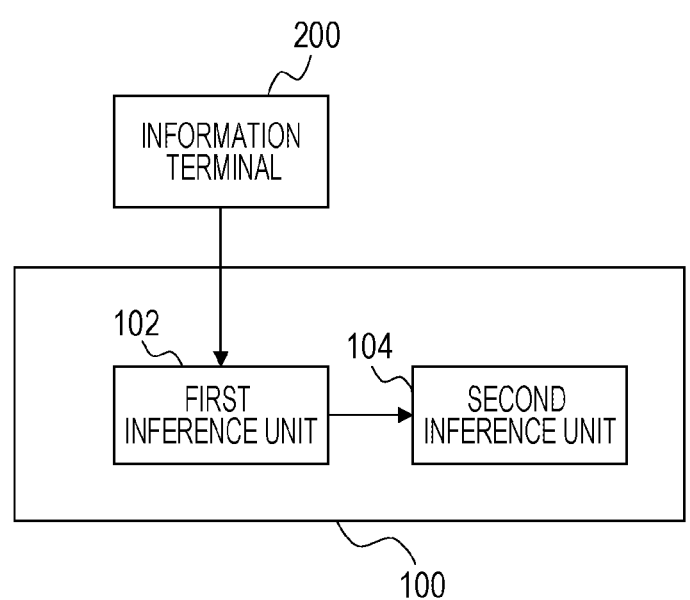
FIG. 1 illustrates an example of a functional configuration of an information processing apparatus.

FIG. 1 illustrates an example of a functional configuration of an information processing apparatus 100 according to the first embodiment. The information processing apparatus 100 according to the present embodiment is connected to an information terminal 200. The information terminal 200 obtains a medical image from a server that is not illustrated in the drawing with regard to a disease corresponding to a diagnostic target. Alternatively, external storage devices such as, for example, an HDD and a DVD drive may be connected, and the information terminal 200 may obtain the medical image from those external storage devices.

Then, the information terminal 200 transmits the medical image to the information processing apparatus 100 via a LAN or the like in accordance with an operation input from a user.

The information processing apparatus 100 includes the first inference unit 102 and the second inference unit 104. The first inference unit 102 performs the first inference to the medical image and obtains the diagnostic name. The second inference unit 104 performs the second inference to the medical image and the diagnostic name and obtains the image finding.

It should be noted that at least part of the respective units in the information processing apparatus 100 illustrated in FIG. 1 may be realized as independent apparatuses. That is, the information processing apparatus including the first inference unit 102 and the information processing apparatus including the second inference unit may also function in cooperation to be realized as an information processing system. Alternatively, the information processing apparatus may also be realized as a virtual server by a virtual technology. The information processing apparatus according to the present invention also includes a mode realized by the plurality of apparatuses described above within its scope. In addition, the information processing apparatus may also be realized as software that realizes each function. According to the present embodiment, it is assumed that the respective units are respectively realized by software.

Figure 2:
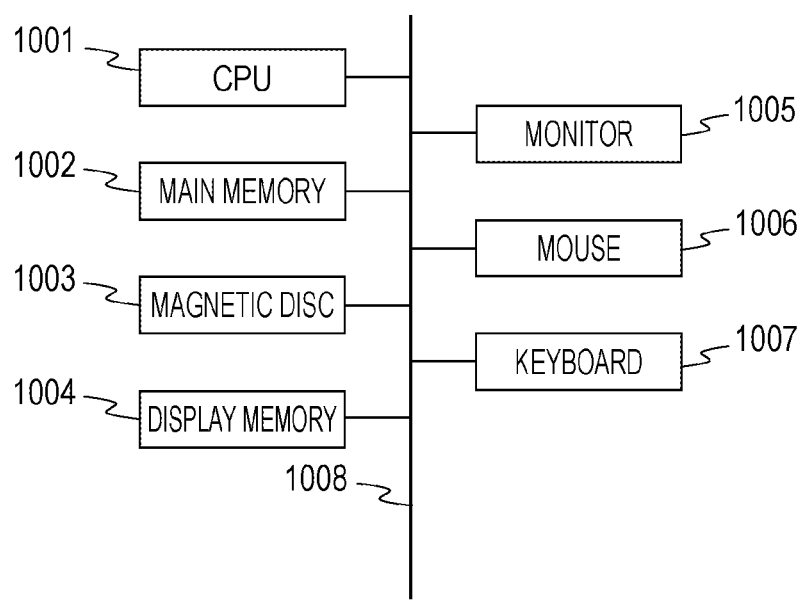
FIG. 2 illustrates an example of a hardware configuration of the information processing apparatus.

FIG. 2 illustrates an example of a hardware configuration of the information processing apparatus 100. In the descriptions, for example, a general-use computer (for example, a PC or a server) is used as the information processing apparatus 100 according to the present embodiment but is not limited to this. A CPU 1001 mainly controls operations of respective components. A main memory 1002 stores a control program executed by the CPU 1001 and provides a work area at the time of program execution by the CPU 1001. A magnetic disc 1003 stores programs for realizing an operating system (OS), a device driver for a peripheral device, and various pieces of application software including programs for performing processing that will be described below and the like. When the CPU 1001 executes the programs stored in the main memory 1002 and the magnetic disc 1003, the functions (software) of the information processing apparatus 100 illustrated in FIG. 1 and processing in a flowchart that will be described below are realized.

A display memory 1004 temporarily stores display data. A monitor 1005 is, for example, a CRT monitor, a liquid crystal monitor, or the like and performs display of an image, a text, or the like on the basis of the data from the display memory 1004. A mouse 1006 and a keyboard 1007 respectively perform pointing input and input of characters and the like by the user. The above-described respective components are connected to one another via a common bus 1008 so as to be mutually communicable.

Figure 3:
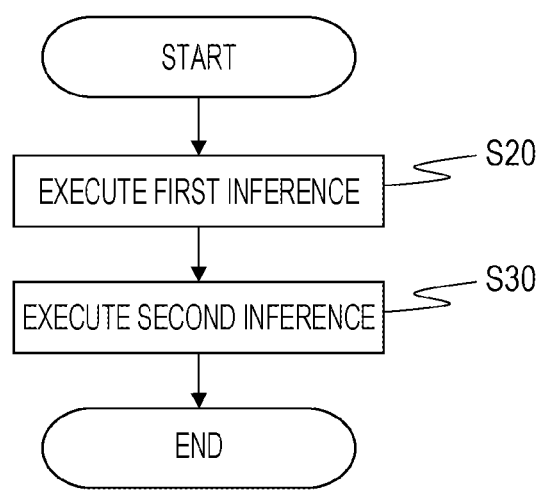
FIG. 3 is a flow chart illustrating an example of processing of the information processing apparatus.

Next, overall processing performed by the information processing apparatus 100 will be described to a flowchart in FIG. 3. FIG. 3 is a flowchart illustrating an example of the processing performed by the information processing apparatus 100. According to the present embodiment, when the CPU 1001 executes the programs for realizing the functions of the respective units which are stored in the main memory 1002, the processing illustrated in FIG. 3 is realized.

In step S20, the first inference unit 102 performs the first inference to the medical image transmitted via the information terminal 200 and obtains the diagnostic name (inferred diagnostic name) of the abnormal shading in the medical image. That is, the first inference unit is equivalent to first inference unit configured to perform the first inference to the medical image data and obtain information related to the first inference result (for example, information related to the diagnostic name identified from the medical image data) which is different from the image finding. According to the present embodiment, the diagnostic name is inferred to an already learnt (learned) Convolutional Neural Network (CNN) as the first inference unit 102. It should be noted that the information related to the first inference result (information related to the diagnostic name) may be a character string indicating the first inference result (diagnostic name) itself or may also be a symbol or a code representing the first inference result (diagnostic name) or a character string obtained by abbreviating the above-described character string.

Figure 4:
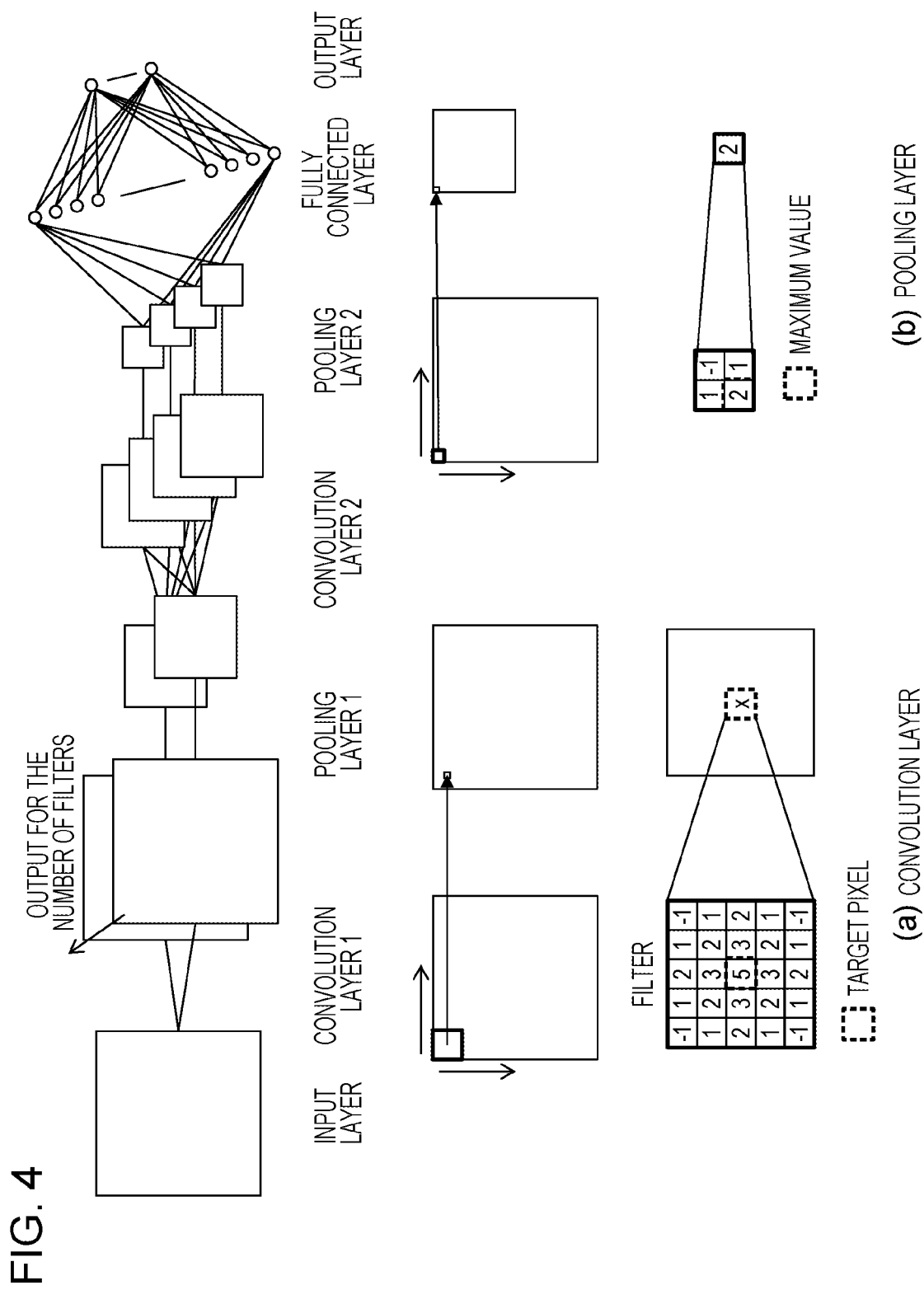
FIG. 4 illustrates an example of first inference unit.

FIG. 4 illustrates an example of the CNN. The CNN is generally constituted by an input layer, an intermediate layer, a fully connected layer, and an output layer. In the input layer, an image normalized to a certain size is input. The intermediate layer is constituted by a plurality of convolution layers (FIG. 4(a)) and a pooling layer (FIG. 4(b)). The convolution layer is a layer where filters are applied to the input to perform convolution, and output values corresponding to the respective filters are obtained. The pooling layer is a layer where one value is output while the plurality of output values are set as input values, and a maximum value of a plurality of input values is set as the output, for example. It should be noted that the output of the convolution layer and the output of the pooling layer may be referred to as a feature map in some cases. The fully connected layer is a layer where the outputs of the intermediate layer are connected to each other, and conversion into a certain number of output values from the feature map is performed. The output layer is constituted by the number of nodes corresponding to the labels set as the targets (herein, the diagnostic names), and a final value is output from the output of the fully connected layer. At this time, in general, the output layer is constituted in a manner that a sum of the output values of the nodes corresponding to the respective labels becomes 1. Then, the label corresponding to the node that takes the maximum output value is output as an inference result. The respective filters and connection weights between the intermediate layer and the fully connected layer and between the fully connected layer and the output layer are learnt (learned) such that an error becomes the minimum from learning data in which the image and a correct label are treated as a set.

Figure 5:
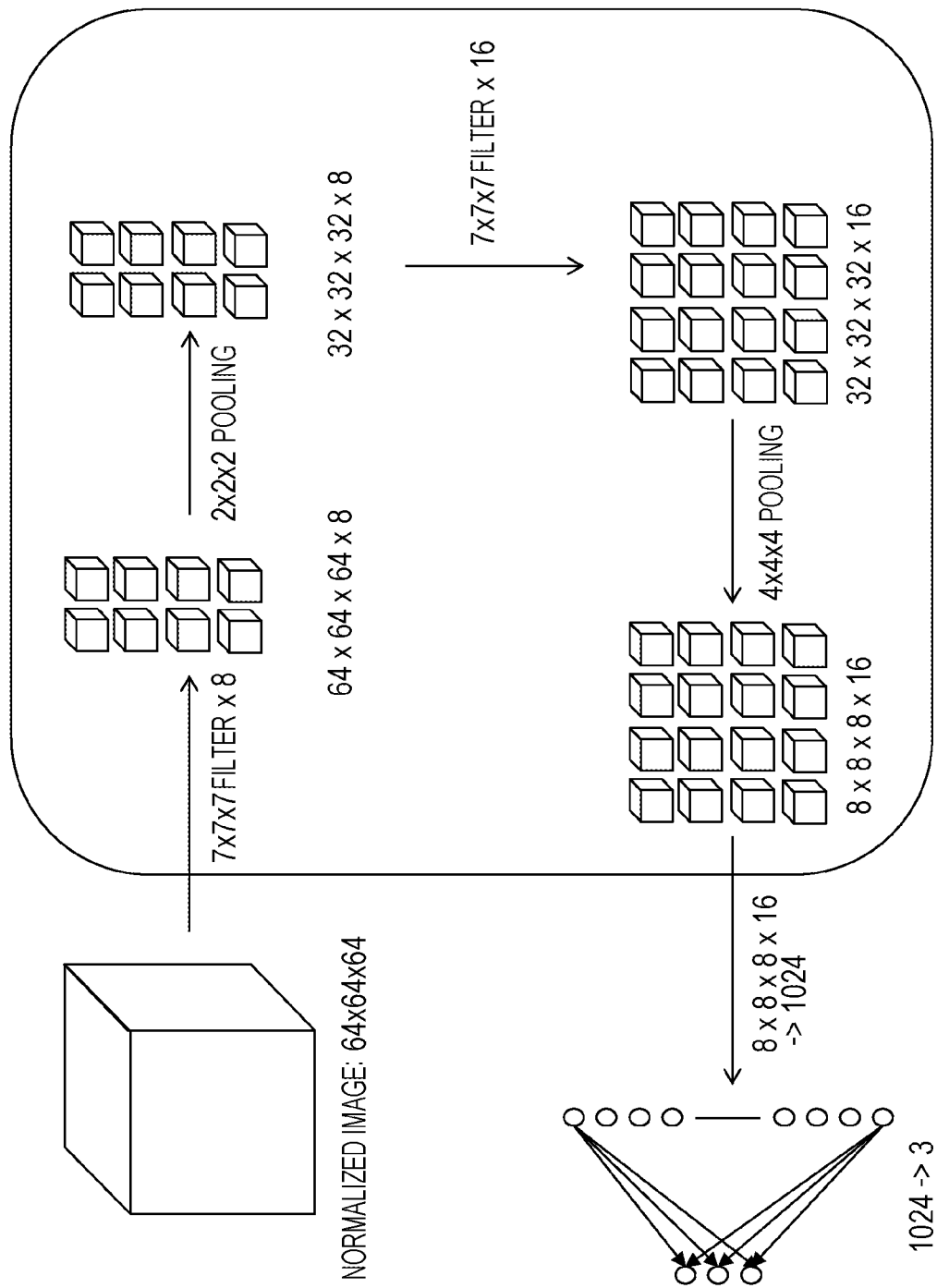
FIG. 5 illustrates an example of a three-dimensional convolutional neural network.

FIG. 5 illustrates an example of the CNN according to the present embodiment. Hereinafter, descriptions will be provided of learning of the CNN which is previously implemented while it is assumed that learning data exists in which values are respectively assigned to the medical images, three-valued diagnostic names (a primary lung cancer, a lung metastasis of a cancer, and a benign tubercle (tumor)), and N image finding items. It should be noted that use of the image finding will be described below in step S30.

Herein, the input is used as being three-dimensional as it is, and the CNN is learnt from a set of the medical image having a size normalized to 64×64×64 and the diagnostic name. The intermediate layer uses two layers each of the convolution layers and the pooling layers and performs conversion into 16 feature maps of 8×8×8. Then, conversion into 1024 node values from the 16 feature maps of 8×8×8 is performed by a network layer in which ReLU (Rectified Linear Unit) is used as an activating function. Finally, classification (inference) of the diagnostic name into the three values from the 1024 node values is performed by a network layer in which a Softmax function is used as the activating function. In general, since the CNN tends to have a higher accuracy as the number of pieces of the learning data is higher, rotation, expansion and contraction, movement, and the like are applied to the medical image to generate new medical images to increase the number of pieces of the learning data. It should be noted that the number of normalized pixels (boxels), the number of stages of the intermediate layer, the fully connected layer, the number of output layers, and the extension of the learning data which have been exemplified are merely examples, and different conditions may of course be used.

At the time of the implementation in step S20, the size is normalized such that the transmitted medical image becomes the same as the input of the above-described CNN, and the normalized image is input to the learnt CNN to obtain the diagnostic name (inferred diagnostic name). For example, inference is performed as to whether the abnormal shading in the medical image is any one of the primary lung cancer, the lung metastasis of the cancer, and the benign tubercle.

In step S30, the second inference unit 104 performs the second inference to the medical image transmitted via the information terminal 200 and the diagnostic name (inferred diagnostic name) obtained in step S20 and obtains the image finding of the above-described medical image. That is, the second inference unit is equivalent to second inference unit configured to perform the second inference to the medical image data and the information related to the first inference result (for example, information related to the diagnostic name) and obtain information related to the image finding as the second inference result. It should be noted that the information related to the image finding may be a character string indicating the image finding itself or may also be a symbol or a code representing the image finding or a character string obtained by abbreviating the above-described character string.

According to the present embodiment, the second inference is performed to the CNN similarly as in step S20. More specifically, the second inference is performed to the learnt CNN for each set of the diagnostic name and the image finding item to obtain the image finding.

Herein, the previously implemented learning of the CNN will be described while a case where a serrated rim is set as the image finding item and values of the serrated rim are to four values of "many", "intermediate", "few", and "none" is used as an example. First, the learning data is divided for each diagnostic name. That is, the learning data is divided into a data group in which the diagnostic name is the primary lung cancer, a data group in which the diagnostic name is the lung metastasis of the cancer, and a data group in which the diagnostic name is the benign tubercle. Next, with respect to the divided data, the CNN is learnt in which the value of the image finding item is set as the correct label, the normalized medical image is set as the input, and the value of the image finding item is set as the output. Herein, the input layer, the intermediate layer, and the fully connected layer in the CNN are set to be similar to those of the CNN illustrated in FIG. 5, and the outputs are set as four values (that is, classified (inferred) into four values from the 1024 nodes. With this configuration, three CNNs in which the values of the serrated rims (four values) are inferred are learnt. At this time, since the learning is independently performed in accordance with the diagnostic name, even in the case of the same image finding, different parameters are learnt in accordance with the diagnostic names (first inference results). Similarly, when the learning of the CNN is performed in the other image finding item too, 3×N CNNs learnt by different parameters for each of the combinations of the diagnostic names (three types according to the present embodiment) and the image finding items (N types according to the present embodiment) are generated.

At the time of the implementation in step S30, the second inference unit 104 obtain s values of the respective image findings to the N CNNs corresponding to the inferred diagnostic names obtained in step S20. That is, the second inference is performed by parameters and/or inference techniques in accordance with the first inference results, and the information related to the image finding is obtained while the medical image is set as the input information. Specifically, further comprising the second inference unit configured to include a classifier that obtains information related to the image finding from the medical image data for each combination of the diagnostic name and the image finding item. Then, the second inference unit configured to obtain the information related to the image finding to the classifier corresponding to the combination including the diagnostic name as the first inference result. For example, in a case where the inferred diagnostic name obtained in step S20 is the primary lung cancer, N pieces of already learnt CNNs corresponding to the primary lung cancer are selected, and the values of the respective image findings are obtained.

In accordance with the present embodiment, the information processing apparatus 100 obtains the inferred diagnostic name from the medical image and obtains the image finding to the medical image and the obtained inferred diagnostic name. According to this, it is possible to obtain the image finding that is further matched with the image finding recalled from the medical image by the doctor. In addition, since the inferred diagnostic name serving as the first inference result is used for the second inference together with the medical image, it is possible to obtain the image finding having a high probability of being matched with the image finding that may be added to an interpretation report in a case where the doctor assumes the diagnostic name and performs the interpretation.

First Modified Example of First Embodiment

According to the present embodiment, in step S20 and step S30, the medical image is used as the input of the CNN, but a region-of-interest of the medical image (that is, a region in the vicinity of a lesion including the lesion) may be obtained, and the obtained region-of-interest may be used as the input of the CNN. It should be noted that the obtaining method for the region-of-interest will be described below according to the second embodiment.

Second Modified Example of First Embodiment

According to the present embodiment, the different CNN is used for each diagnostic name in step S30, but different CNNs are not necessarily used for all the diagnostic names. For example, a common CNN may exist for a plurality of diagnostic names. For example, a common CNN is used for the primary lung cancer and the lung metastasis of the cancer, and a CNN for the benign tubercle may be used for the benign tubercle. According to this, since a CNN in accordance with a feature of the abnormal shading can be used, it is possible to obtain the image finding that is further matched with the image finding recalled from the medical image by the doctor.

Third Modified Example of First Embodiment

According to the present embodiment, the second inference is performed to the inferred diagnostic names obtained in step S20 to obtain the image finding in step S30, but the second inference may be performed to a diagnostic name obtained by the other technique to obtain the image finding. For example, the diagnostic name input via the information terminal 200 by the doctor may be obtained and used. According to this, since the second inference can be performed to the diagnostic name that is thought about by the doctor, it is possible to obtain the image finding that is further matched with the image finding recalled from the medical image by the doctor.

Second Embodiment

The information processing apparatus 100 according to the present embodiment obtains a region-of-interest from the medical image to perform image processing and obtains and presents an inferred diagnostic name of the abnormal shading in the region-of-interest and an image finding to a first image feature amount obtained as a result of the image processing.

Figure 6:
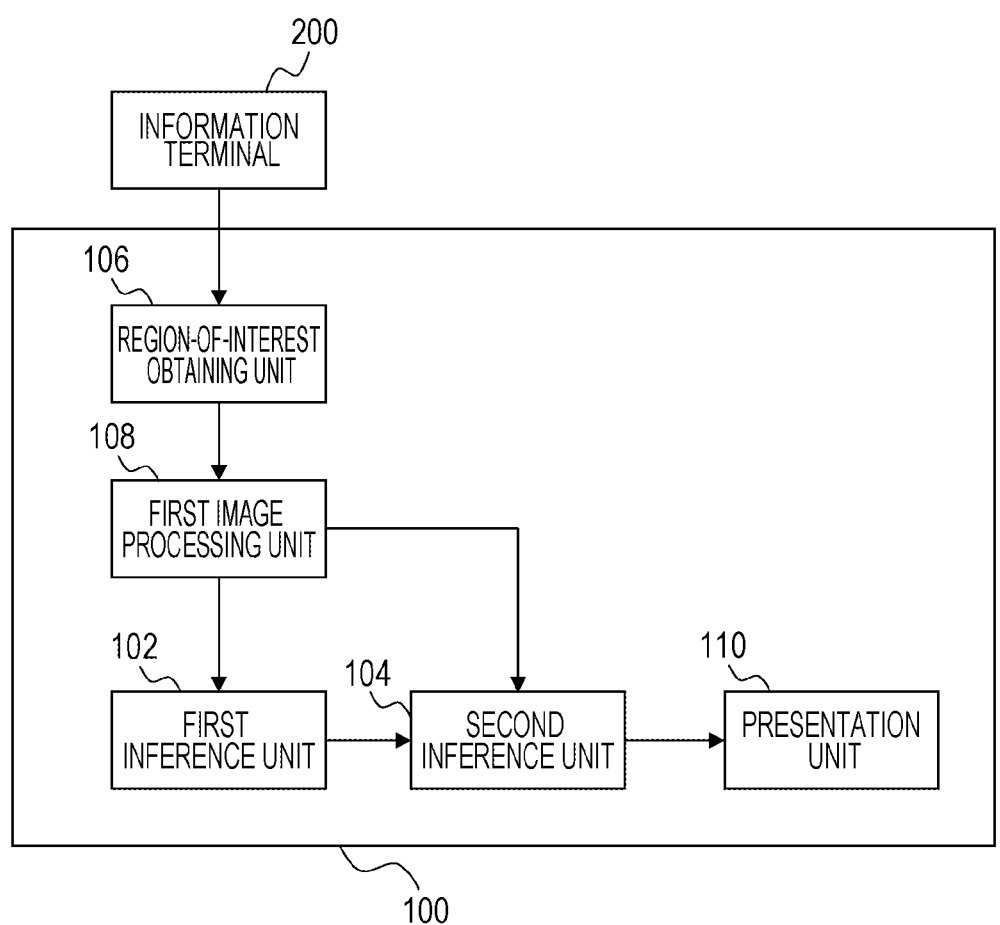
FIG. 6 illustrates another example of the hardware configuration of the information processing apparatus.

FIG. 6 illustrates an example of a functional configuration of the information processing apparatus 100 according to the present embodiment. It should be noted that only different parts from the first embodiment will be described with regard to component parts assigned with the same reference signs as those in FIG. 1.

The information processing apparatus 100 includes a region-of-interest obtaining unit 106, a first image processing unit 108, the first inference unit 102, the second inference unit 104, and a presentation unit 110. The region-of-interest obtaining unit 106 obtains a region-of-interest corresponding to a target of the image processing from the medical image. The first image processing unit 108 performs the image processing on the region-of-interest and calculates the first image feature amount. The first inference unit 102 obtains the inferred diagnostic name of the abnormal shading in the region-of-interest to the first image feature amount. The second inference unit 104 obtains the image finding in the region-of-interest to the first image feature amount and the inferred diagnostic name. The presentation unit 110 presents the obtained image finding.

The hardware configuration of the information processing apparatus 100 is similar to FIG. 2 according to the first embodiment.

Figure 7:
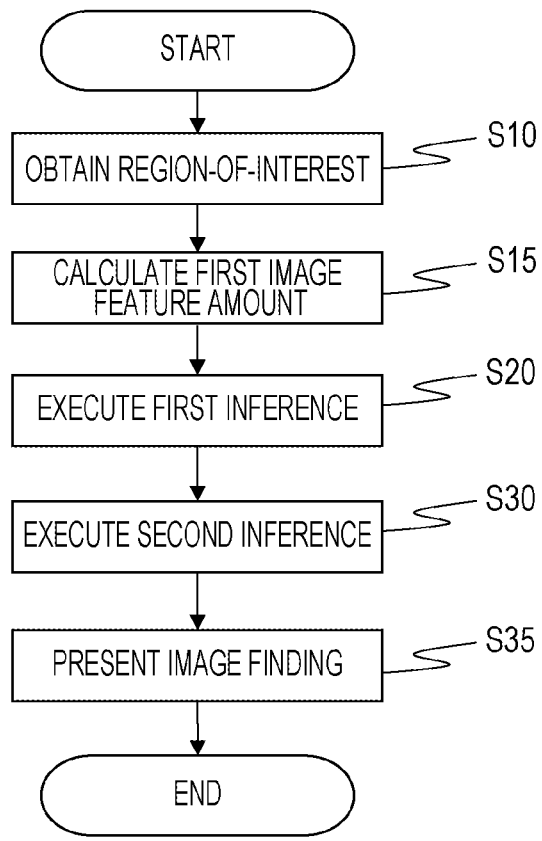
FIG. 7 is a flow chart illustrating another example of the processing of the information processing apparatus.

Next, the overall processing performed by the information processing apparatus 100 will be described to a flowchart in FIG. 7. It should be noted that only different parts from the first embodiment will be described with regard to the processing assigned with the same reference sign as that in FIG. 3.

In step S10, the region-of-interest obtaining unit 106 obtains the region-of-interest from the medical image transmitted via the information terminal 200. According to the present embodiment, it is assumed that a rectangular region set by the user to a Viewer on the information terminal 200 is further transmitted from the information terminal 200, and the transmitted rectangular region is obtained as the region-of-interest. It should be noted that other examples will be described according to third and fourth embodiments.

In step S15, the first image processing unit 108 calculates the first image feature amount from the region-of-interest obtained in step S10. That is, the first image processing unit is equivalent to first image processing unit configured to perform the image processing on the medical image data and obtain the first image feature amount. The image feature amount calculated herein may be any feature amount, but according to the present embodiment, the image feature amount is obtained as follows. First, an abnormal shading region is further extracted from the region-of-interest to a known segmentation technology (such as threshold processing, a region expansion method, a Level-set method, or a Graph-cut method). Then, a general statistics value such as an average value of luminances (densities) in the extracted abnormal shading region, a variance, a kurtosis, or a skewness is calculated as the image feature amount.

Of course, image feature amounts calculated by other method may also be used. For example, the CNN may be learnt in which the normalized region-of-interest is set as the input and the correct label is set as the diagnostic name, and the output value of the fully connected layer may be used as the image feature amount.

In step S20, the first inference unit 102 performs the first inference to the first image feature amount calculated in step S15 and obtains the inferred diagnostic name of the abnormal shading in the region-of-interest. According to the present embodiment, the inferred diagnostic name is obtained to an already learnt support vector machine (SVM) as the first inference unit 102.

Herein, the learning of the first inference unit 102 is previously performed as follows. It should be noted that the data described according to the first embodiment is used as the learning data, but the region-of-interest is further added to the medical image by a manual operation. First, the image feature amount is extracted by the same method as the method in step S15 with respect to the added region-of-interest. Then, the support vector machine is learnt which obtains the diagnostic name from the pair of the extracted image feature amount and the diagnostic name.

Herein, the descriptions have been provided while the SVM is used, but of course, the other inference technique such as a neural network or a Bayesian network may be learnt, and the diagnostic name may be obtained to the learnt inference technique.

In step S30, the second inference unit 104 performs the second inference to the first image feature amount calculated in step S15 and the inferred diagnostic names obtained in step S20 and obtains the image finding in the region-of-interest.

According to the present embodiment, for each item of the diagnostic name and the image finding, the value of the image finding is obtained to the same inference technique, specifically, the already learnt Random Forest classifier. Of course, other known techniques such as the neural network, the support vector machine, and the Bayesian network may also be used as the inference technique.

At this time, the learning of the second inference unit 104 is previously performed as follows. It should be noted that, in the learning data, the region-of-interest is added to the medical image similarly as in the explanation in step S20, and the image feature amount is calculated by the same method as step S15. Herein, first, a data group having the same label (for example, the primary lung cancer) is extracted from the learning data. Next, the Random Forest classifiers are learnt while the sets of the image feature amounts of the respective data and the values of the image findings added to the data (for example, the serrated rim) are treated as the learning data. Similarly as in the first embodiment, since the learning is independently performed in accordance with the diagnostic name, different parameters are learnt in accordance with the diagnostic names (first inference results) even in the case of the same image finding item. Finally, 3×N pieces of the Random Forest classifiers are learnt.

At the time of the implementation in step S30, the second inference unit 104 obtains the values of the respective image findings to the N Random Forest classifiers corresponding to the diagnostic names obtained in step S20 while the first image feature amount in the region-of-interest obtained in step S15 is set as the input information. That is, the image findings are obtained by the parameters and/or the inference techniques in accordance with the first inference results while the medical image is set as the input information. For example, in a case where the diagnostic name obtained in step S20 is the primary lung cancer, the N already learnt Random Forest classifiers corresponding to the primary lung cancer are selected, and the values of the respective image findings are obtained.

In step S35, the presentation unit 110 presents the diagnostic names obtained in step S20 and the image findings obtained in step S30 to the user as aid information.

In accordance with the present embodiment, the information processing apparatus 100 obtains the region-of-interest from the medical image and performs the image processing on the region-of-interest to calculate the first image feature amount. Then, the inferred diagnostic name is obtained to the calculated first image feature amount, and the image finding is obtained on the basis of the obtained inferred diagnostic name and the first image feature amount. Therefore, the image finding that is further matched with the image finding recalled from the feature related to the region-of-interest of the medical image can be presented as the aid information.

First Modified Example of Second Embodiment

According to the present embodiment, in step S30, the obtainment of the image finding is performed to the same inference technique with respect to the inferred diagnostic name (first inference result). However, the same inference technique does not necessarily need to be used. For example, different inference techniques in accordance with the diagnostic names may be used such as the Random Forest classifier in the case of the primary lung cancer and the support vector machine in the case of the lung metastasis of the cancer. In addition, different inference techniques may be used in accordance with the image finding items. Furthermore, different inference techniques may be used in accordance with pairs of the diagnostic names and the image findings.

In addition, according to the present embodiment, the obtainment of the image finding is performed while the image feature amount is set as the input for each of all the diagnostic names and the image finding items, but the configuration does not necessarily need to be the above. Specifically, the obtainment based on the CNN may be performed to the medical image in part of the diagnostic names and image finding items similarly as in the first embodiment, and the obtainment may be performed to the image feature amount in the other diagnostic names and image findings.

Furthermore, the inferred diagnostic name may be obtained by the CNN in step S20, and the image finding may be obtained to the image feature amount in step S30. Of course, in this case too, the image finding may be obtained by the above-described various combinations in step S30.

In accordance with the above-described method, since the most appropriate inference technique can be applied to each inferred diagnostic name or combination of the inferred diagnostic name and the image finding item, the more appropriate image finding can be obtained.

Third Embodiment

The information processing apparatus 100 according to the present embodiment obtains a likelihood of a malignancy of the target disease drawn on the medical image as the first inference result on the basis of the first image feature amount obtained by applying the image processing to the region-of-interest. That is, the information related to the first inference result is information related to the likelihood of the malignancy of the disease identified from the medical image data. Then, the image finding in the region-of-interest is obtained while the obtained likelihood of the malignancy and the first image feature amount are set as the input of the second inference unit. It should be noted that the information related to the likelihood of the malignancy of the disease may be a character string indicating the likelihood of the malignancy of the disease or may also be a symbol or a code representing the likelihood of the malignancy of the disease or a character string obtained by abbreviating the above-described character string.

The information processing apparatus 100 according to the present embodiment is constituted by a functional configuration similar to FIG. 6 according to the second embodiment. In addition, a flowchart for describing the overall processing performed by the information processing apparatus 100 is similar to FIG. 7. It should be noted however that part of the processing is different from the second embodiment. Hereinafter, with regard to the overall processing performed by the information processing apparatus 100 according to the present embodiment, only different parts from the second embodiment will be described with reference to the flowchart in FIG. 7.

The processing in steps S10 and S15 is similar to the processing according to the second embodiment.

In step S20, the first inference unit 102 obtains the likelihood of the malignancy of the target disease drawn to the first image feature amount calculated in step S15. The first inference unit 102 may use any technique (such as a regression expression) with which the likelihood can be obtained but use the Bayesian network herein to obtain the likelihood of the malignancy of the target disease.

It should be noted that, at the time of the learning, conversion into two-value category values in which the primary lung cancer and the lung metastasis of the cancer are set as malignant, and the benign tubercle is set as benign may be performed to perform the learning, and an inference probability with respect to the malignancy may be output as the likelihood at the time of the obtainment.

In step S30, the second inference unit 104 obtains the image finding to the first image feature amount calculated in step S15 and the likelihood of the malignancy inferred in step S20.

According to the present embodiment, the first image feature amount and the likelihood are set as the inputs to the second inference unit, and the values of the respective image findings are obtained by the inference technique learnt for each image finding item. Herein, various known techniques such as the neural network and the support vector machine can be used for the obtainment of the image finding.

It should be noted that, at the time of the learning, while the likelihood is set as 1.0 in the case of the primary lung cancer and the lung metastasis of the cancer and the likelihood is set as 0 in the case of the benign tubercle, the learning may be performed.

In accordance with the present embodiment, the information processing apparatus 100 uses the likelihood of the malignancy with respect to the abnormal shading in the region-of-interest as one of the inputs to the second inference unit and obtains the image finding by taking the likelihood of the malignancy into account by the second inference unit. Therefore, the image finding that is further matched with the image finding recalled from the feature related to the region-of-interest of the medical image can be presented as the aid information.

First Modified Example of Third Embodiment

According to the present embodiment, the parameter of the inference technique is determined by the learning in step S30. However, the parameter does not necessarily need to be set by the learning alone. For example, the parameter may be manually adjusted such that influences by the likelihood of the malignancy on the obtainment result (that is, the value of the image finding) are increased.

In accordance with the above-described method, since the influences imparted on the obtainment result by the feature obtained from the region-of-interest can be set to be further increased, the image finding that is further matched with the image finding recalled from the feature related to the region-of-interest of the medical image can be presented as the aid information.

Second Modified Example of Third Embodiment

According to the present embodiment, the likelihood of the malignancy is obtained in step S20, and the image finding is obtained in step S30 to the likelihood of the malignancy inferred in step S20. However, the likelihood inferred in step S20 does not necessarily need to be the likelihood of the malignancy. For example, it may also be a likelihood of a benignancy or other likelihoods.

Fourth Embodiment

The information processing apparatus 100 according to the present embodiment applies further image processing in accordance with the first inference result (likelihood of the malignancy) to the region-of-interest to calculate a second image feature amount (shape feature amount such as a shape of a contour or a length of a straight line of the contour). Then, the image finding is obtained on the basis of the calculated second image feature amount.

Figure 8:
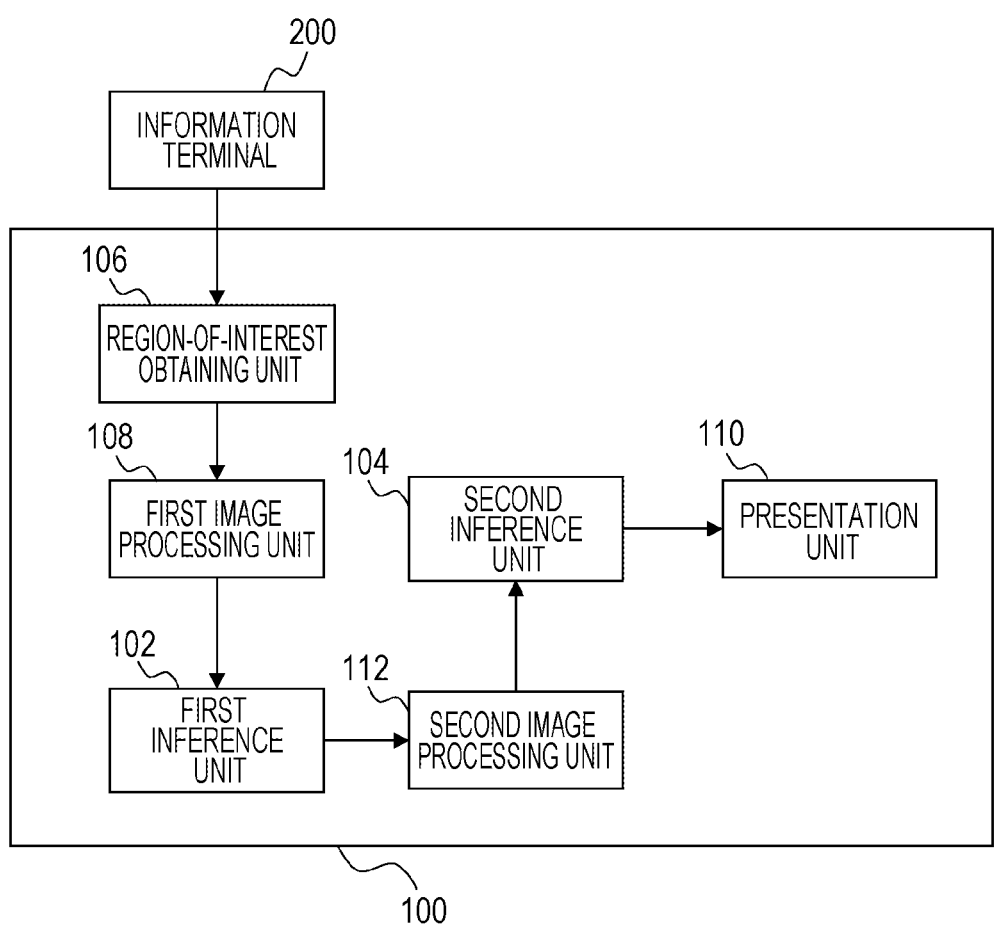
FIG. 8 illustrates still another example of the hardware configuration of the information processing apparatus.

FIG. 8 illustrates an example of a functional configuration of the information processing apparatus 100 according to the present embodiment. It should be noted that only different parts from the second and third embodiments will be described with regard to component parts assigned with the same reference signs as those in FIG. 6.

The information processing apparatus 100 includes the region-of-interest obtaining unit 106, the first image processing unit 108, the first inference unit 102, a second image processing unit 112, the second inference unit 104, and the presentation unit 110.

Since the region-of-interest obtaining unit 106, the first image processing unit 108, the first inference unit 102, and the presentation unit 110 are the same functions as the second and third embodiments, descriptions thereof will be omitted.

The second image processing unit 112 performs the image processing in accordance with the first inference result (likelihood of the malignancy).

The second inference unit 104 obtains the image finding to the second image feature amount (the shape of the contour or the length of the straight line of the contour).

The hardware configuration of the information processing apparatus 100 is similar to FIG. 2 according to the first to third embodiments.

Figure 9:
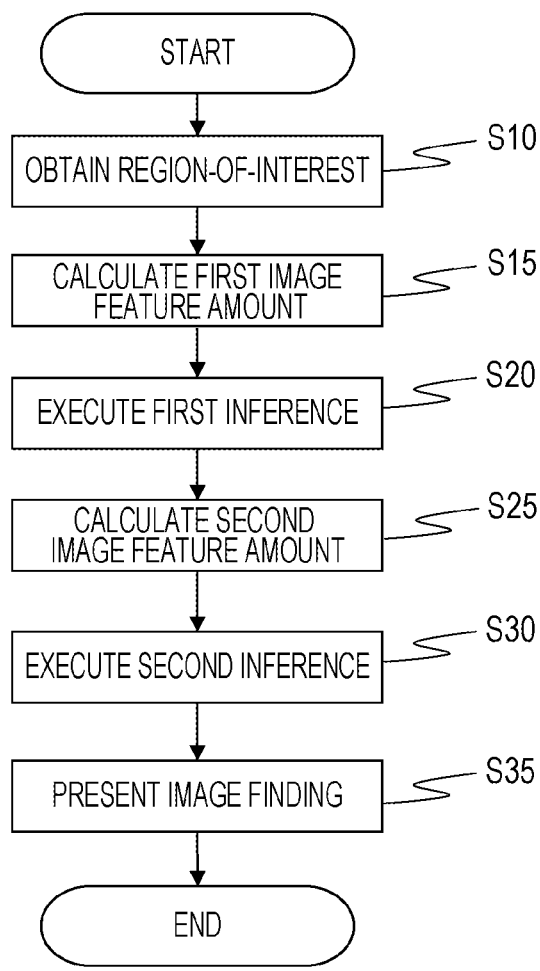
FIG. 9 is a flow chart illustrating still another example of the processing of the information processing apparatus.

Next, the overall processing performed by the information processing apparatus 100 will be described to a flowchart in FIG. 9. It should be noted that only different parts from the third embodiment will be described with regard to the processing assigned with the same reference sign as that in FIG. 7.

The processing in steps S10 to S20 is similar to the processing according to the third embodiment.

In step S25, the second image processing unit 112 performs the image processing in accordance with the obtained likelihood of the malignancy in step S20 and calculates the second image feature amount. That is, the second image processing unit is equivalent to second image processing unit configured to perform the image processing in accordance with the first inference result on the medical image data and obtain the second image feature amount. Specifically, the shape feature amount such as the shape of the contour or the length of the straight line of the contour is calculated.

Figure 10A:
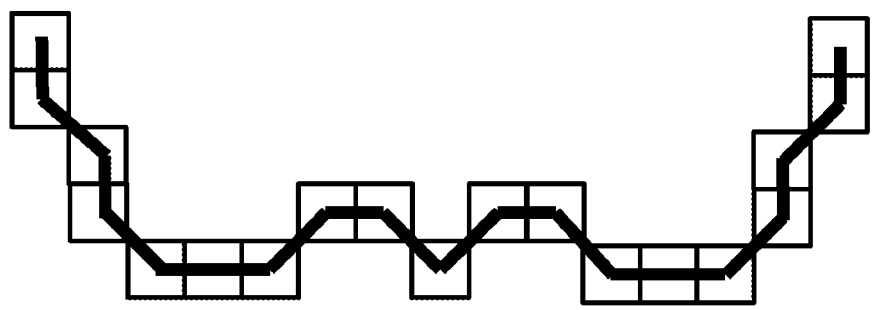
FIG. 10A illustrates an example of processing of a second image processing unit.
Figure 10B:
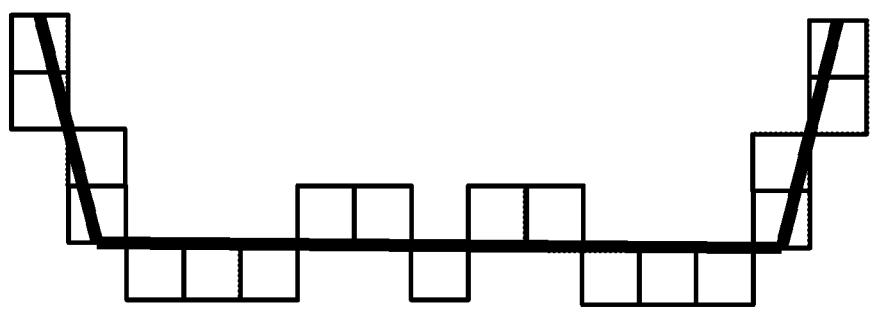
FIG. 10B illustrates an example of the processing of the second image processing unit.

An example of the calculation will be described to FIGS. 10A and 10B. It is supposed that contours as illustrated in FIGS. 10A and 10B are extracted in the image processing in step S15. In this example, curvatures in the respective pixels (boxels) are calculated, and whether or not the contour is a straight line is determined in accordance with the curvature, and a length of the straight line is measured.

In a case where the likelihood of the malignancy calculated in step S20 is higher than a predetermined value (for example, 0.3), it is determined that the line is curved in a case where the curvature exceeds a threshold. As a result, conversion into the contour like a bold line A is performed, and the length of the straight line is measured on the basis of this to be set as the feature amount. On the other hand, in a case where the likelihood of the malignancy is lower than or equal to the predetermined value, the threshold with respect to the curvature is increased, and even when the curvature is high to some extent, the contour is regarded as the straight line as it is. As a result, conversion into the contour like a bold line B is performed, and the length of the straight line is measured on the basis of this to be set as the feature amount. This is an imitation where the doctor tends to regard even a rough outline of the same contour as the straight line in a case where the likelihood of the benignancy is high in general (that is, the likelihood of the malignancy is low).

In this manner, in step S25, the image processing in accordance with the likelihood of the malignancy (that is, the first inference result) is performed, and the second image feature amount is calculated.

In step S30, the second inference unit 104 obtains the image finding while the second image feature amount calculated in step S25 is set as the input. Similarly as in the third embodiment, various known techniques such as the neural network and the support vector machine can be used for the inference of the image finding herein.

The processing in step S35 is similar to the processing according to the third embodiment.

In accordance with the present embodiment, the information processing apparatus 100 calculates the second image feature amount in accordance with the likelihood of the malignancy (first inference result) and obtains the image finding while the second image feature amount is set as the input. That is, the image finding inferred on the basis of the image feature amount in which a thought process by the doctor is taken into account is presented. Therefore, the image finding that is further matched with the image finding recalled from the feature related to the region-of-interest of the medical image can be presented as the aid information.

First Modified Example of Fourth Embodiment

According to the present embodiment, in step S30, the image finding is obtained while only the calculated second image feature amount is set as the input. However, the image finding may be obtained to the first image feature amount as well. Furthermore, similarly as in the third embodiment, the image finding may be obtained by adding the likelihood of the malignancy as the feature amount.

Other Embodiments

The present invention can also be realized by processing in which a program that realizes one or more functions of the above-described embodiments is supplied to a system or an apparatus via a network or a storage medium, and one or more processors in a computer of the system or the apparatus read out the program to be executed. In addition, the present invention can also be realized by a circuit (for example, an ASIC) that realizes one or more functions.

It should be noted that the above-described embodiments are merely specific examples when the present invention is carried out, and a technical scope of the present invention is not to be restrictively interpreted by these. That is, the present invention can be carried out in various forms without departing from the technical concept and the main features. In addition, combinations of the respective embodiments are also included in the technical scope of the present invention.

According to the present invention, it becomes possible to obtain the information related to the image finding with which the interpretation by the doctor can be appropriately aided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus characterized by comprising:
   a memory storing a program; and
   one or more processors which, by executing the program, function as
   first inference means for performing a first inference on medical image data by using the medical image data as an input to a first classifier and obtaining information representing a diagnosis name identified from the medical image data as a first inference result; and
   second inference means for performing a second inference on the medical image data and on the information representing the diagnosis name by using a second classifier and obtaining information representing an image finding as a second inference result, wherein the information representing the image finding is a semantic description of one or more features in the medical image data.

2. The information processing apparatus according to claim 1, wherein the second inference means infer the second inference result by a parameter and/or an inference technique in accordance with the first inference result.

3. The information processing apparatus according to claim 1, wherein the second inference means
   includes a respective classifier for obtaining the information representing the image finding for each combination of the diagnosis name and an item of the image finding, and
   is configured to obtain the information representing the image finding by using the classifier corresponding to the combination including the diagnosis name serving as the first inference result.

4. The information processing apparatus according to claim 1, wherein the one or more processors, by executing the program, further function as:
   a first image processing unit configured to perform image processing on the medical image data and obtain a first image feature amount,
   wherein the first inference means is configured to perform the first inference by using the first image feature amount as an input to the first classifier, and
   wherein the second inference means is configured to perform the second inference by using the first image feature amount and the first inference result as inputs to the second classifier.

5. The information processing apparatus according to claim 1, wherein the second inference means selects the second classifier from among a plurality of second classifiers based on the information representing the diagnosis name,
   wherein the diagnosis name is selected from a set of selectable diagnosis names, and wherein, for each selectable diagnosis name from the set of selectable diagnosis names, the plurality of second classifiers include a respective second classifier for each pairwise combination of the selectable diagnosis name and image-finding item of the image finding.

6. The information processing apparatus according to claim 5, wherein the image finding includes two or more image-finding items, and
wherein the second inference means selects, from among the plurality of second classifiers, the two or more second classifiers that correspond to the two or more image-finding items and to the diagnosis name and uses the two or more second classifiers to obtain the information representing the image finding.

7. The information processing apparatus according to claim 6, wherein each second classifier of the plurality of second classifiers includes a respective Random Forest classifier, neural network, support vector machine, or Bayesian network.

8. The information processing apparatus according to claim 1, wherein the second inference means inputs the information representing the diagnosis name and the medical image data to the second classifier and infers the information representing the image finding.

9. The information processing apparatus according to claim 1, wherein the one or more processors, by executing the program, further cause the information processing apparatus to add the image finding to a medical report, wherein the medical report also includes image findings that were entered by a physician.

10. The information processing apparatus according to claim 1, wherein the information representing the image finding includes two or more image-finding items.

11. An information processing apparatus characterized by comprising:
a memory storing a program; and
one or more processors which, by executing the program, function as
first inference means for performing a first inference on medical image data by using the medical image data as an input to a first classifier and obtaining information representing a likelihood of a malignancy of a disease identified from the medical image data as a first inference result; and
second inference means for performing a second inference on the medical image data and on the information representing the likelihood of the malignancy of the disease by using a second classifier and obtaining information representing an image finding as a second inference result, wherein the information representing the image finding is a semantic description of one or more features in the medical image data.

12. The information processing apparatus according to claim 11, wherein the second inference means infer the second inference result by a parameter and/or an inference technique in accordance with the first inference result.

13. The information processing apparatus according to claim 11, wherein the one or more processors, by executing the program, further function as:
a first image processing unit configured to perform image processing on the medical image data and obtain a first image feature amount,
wherein the first inference means is configured to perform the first inference by using the first image feature amount as an input to the first classifier, and
wherein the second inference means is configured to perform the second inference by using the first image feature amount and the first inference result as inputs to the second classifier.

14. The information processing apparatus according to claim 11, wherein the one or more processors, by executing the program, further function as:
a second image processing unit configured to perform image processing in accordance with the first inference result on the medical image data and obtain a second image feature amount,
wherein the second inference means is configured to perform the second inference by using the second image feature amount as an input to the second classifier.

15. A control method for an information processing apparatus, the control method comprising:
performing a first inference on medical image data by using the medical image data as an input to a first classifier and obtaining information representing a diagnosis name identified from the medical image data as a first inference result; and
performing a second inference on the medical image data and on the information representing the diagnosis name by using a second classifier and obtaining information representing an image finding as a second inference result, wherein the information representing the image finding is a semantic description of one or more features in the medical image data.

16. A non-transitory computer-readable storage medium storing a program for causing a computer to execute a control method for an information processing apparatus, the control method comprising:
performing a first inference on medical image data by using the medical image data as an input to a first classifier and obtaining information representing a diagnosis name identified from the medical image data as a first inference result; and
performing a second inference on the medical image data and on the information representing the diagnosis name by using a second classifier and obtaining information representing an image finding as a second inference result, wherein the information representing the image finding is a semantic description of one or more features in the medical image data.

17. A control method for an information processing apparatus, the control method comprising:
performing a first inference on medical image data by using the medical image data as an input to a first classifier and obtaining information representing a likelihood of a malignancy of a disease identified from the medical image data as a first inference result; and
performing a second inference on the medical image data and on the information representing the likelihood of the malignancy of the disease by using a second classifier and obtaining information representing an image finding as a second inference result, wherein the information representing the image finding is a semantic description of one or more features in the medical image data.

18. A non-transitory computer-readable storage medium storing a program for causing a computer to execute a control method for an information processing apparatus, the control method comprising:
performing a first inference on medical image data by using the medical image data as an input to a first classifier and obtaining information representing a likelihood of a malignancy of a disease identified from the medical image data as a first inference result; and performing a second inference on the medical image data and on the information representing the likelihood of the malignancy of the disease by using a second classifier and obtaining information representing an image finding as a second inference result, wherein the information representing the image finding is a semantic description of one or more features in the medical image data.

* * * * *